United States Patent [19]

Brem et al.

[11] Patent Number: 5,639,457

[45] Date of Patent: Jun. 17, 1997

[54] PROCESS FOR THE PRODUCTION OF ANTIBODIES

[75] Inventors: Gottfried Brem, Larezhausen, D-8893 Hilgertshausen; Ulrich Weidle, München, both of Germany

[73] Assignee: Gottfried Brem, Hilgertshausen, Germany

[21] Appl. No.: 341,888

[22] Filed: Nov. 15, 1994

Related U.S. Application Data

[63] Continuation of Ser. No. 133,781, Oct. 8, 1993, abandoned, which is a continuation of Ser. No. 639,605, Jan. 10, 1991, abandoned.

[30] Foreign Application Priority Data

Jan. 15, 1990 [DE] Germany .................. 40 00 939.4

[51] Int. Cl.$^6$ .................. C12N 15/00; A61K 39/00
[52] U.S. Cl. .................. 424/184.1; 800/2; 800/DIG. 1; 800/DIG. 4; 435/172.3
[58] Field of Search ........................................... 800/2

[56] References Cited

U.S. PATENT DOCUMENTS

| | | | |
|---|---|---|---|
| 4,642,334 | 2/1987 | Mone et al. | 530/388 |
| 4,870,009 | 9/1989 | Evans et al. | 435/70 |

OTHER PUBLICATIONS

Proceedings of the National Academy of Sciences of the U.S.A., Band 85 No. 9, May 1988, pp. 3130–3134.
Brem et al, Production of transgenic mice, rabbits and pigs by microinjection into pronuclei, Zuchthygiene, Jan. 20, 1985.
Hammer et al, Nature, Production of transgenic rabbits, sheep and pigs by microinjection, vol. 315, Jun. 20, 1985.
Bruggemann et al J. Exp. Med 166: 1351, 1987.
Weidle et al Gene 98: 185, 1991.
Hanner et al Nature 315: 680, 1985.
Kocks et al PNAS 85: 8206, 1988.
Jaenisch et al Science 240: 1470, 1988.
Lenz et al Gene 87: 213, 1990.

*Primary Examiner*—Suzanne E. Ziska
*Attorney, Agent, or Firm*—Nikaido, Marmelstein, Murray & Oram LLP

[57] ABSTRACT

Process for the production of proteins with antibody activity in which one or several DNA sequences coding for this protein are introduced into the male pronucleus of a fertilized ovum of a pig or rabbit by microinjection, the ova are implanted in the oviduct of a pig or rabbit, the offspring are bred and the protein with antibody activity is isolated from their serum in the usual way whereby the DNA sequences used for the microinjection are free of bacterial foreign sequences, and are preferably used with immunoglobulin promoter and enhancer sequences.

10 Claims, 1 Drawing Sheet

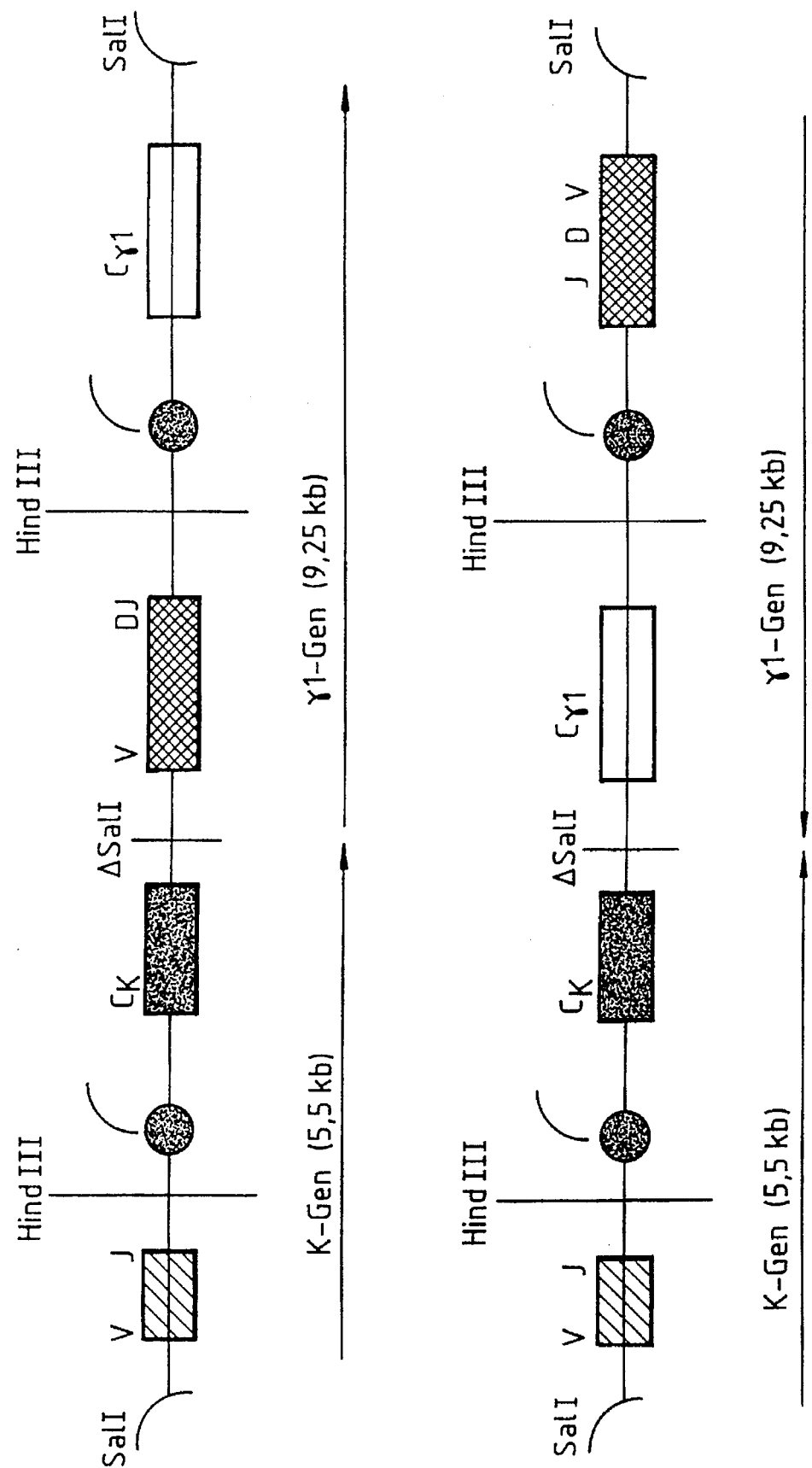

PROCESS FOR THE PRODUCTION OF ANTIBODIES

This application is a continuation of application Ser. No. 08/133,781 filed Oct. 8, 1993, now abandoned, which is a continuation of application Ser. No. 07/639,605 filed Jan. 10, 1991, now abandoned.

DESCRIPTION

In order to express foreign DNA sequences in animals one can inject the DNA in the male pronucleus of fertilized ova by microinjection, then implant the ova in the oviduct of corresponding animals and breed the offspring which express the microinjected genetic material. In mice, transgenic animals have also been produced by retrovirus infection of embryos or by transfer of genetically manipulated stem cells into blastocytes (Jänisch, R.: Science 240, 1468 (1988); Palmiter, R. D. and Brinster, Ann. Rev. Genet. 20, 465 (1986); R. L. Brinster and R. D. Palmiter, Harvey Lectures, Series 80 (Liss, New York, 1986), pp 1–38).

Meanwhile the introduction of foreign genetic information into germ lines has been described for a series of species. Thus, for example for chicken (Bosselman et al., Science 243, 533 (1989)), fish (Brem, G., Brenig, B., Hoerstgen-Schwark, G., and Winnacker, E. L.: Aquaculture 68, 209 (1988)), rabbits (R. E. Hammer et al., Nature 315, 680 (1985); G. Brem et al., Zuchthygiene 20, 251 (1985)), sheep (A. J. Clark et al., Bio/Technology 7, 487 (1989); J. Simons et al., Bio/Technology 6, 179 (1988); C. E. Rexroad, Jr. et al., Mol. Reprod. Dev. 1, 164 (1989)) and pigs (G. Brem et al., Zuchthygiene 20, 251 (1985); K. M. Ebert et al., Mol. Endocrinol. 2, 277 (1988); Brem, G., Brenig, B., M üller, M., KräuBlich, H. and Winnacker, E. L.: Occ. Publ. Br. Soc. Anim. Prod. 12 (1988) 15–31).

The rabbit c-myc gene was expressed in rabbits under the control of regulatory sequences of an immunoglobulin gene which resulted in the induction of leukaemia in transgenic rabbits (Knight, K. L., Spicker-Polat, H., Kazdin, D., Oi, V. T.: Proc. Natl. Acad. Sci. USA 85 (1988) 3130–3134).

Transgenic rabbits have also been produced which express the human somatrotrophin gene (Enikolopov et al., Dokl. Acad. Nauk SSSR, 299 (1988) 1246–1249). The expression of the "human growth hormone releasing factor" in transgenic rabbits has also been described (Gazaryan et al., Dokl. Acad. Nauk SSSR 305 (1989) 726–728).

The expression of bovine growth hormone in transgenic pigs has been demonstrated and the effect on the growth of the transgenic animals has been investigated (J. Anim. Sci. 66 (suppl. 1) 267 (1988)).

Transgenic pigs have also been produced which express the surface antigen of the human hepatitis B virus (Dokl. Akad. Nauk SSSR 306 (1989) 206–209).

Genes for the light and for the heavy chain of antibodies with defined specificity (directed towards nitrophenol, trinitrophenol, phosphorylcholine) were isolated from the respective hybridoma lines and introduced into the germ line of mice. The genes for the light and heavy chain were expressed in the respective transgenic mice in the form of a recombinant antibody (Rusconi, S. and Köhler, G.: Nature 314, 330 (1985; Grosschedl, R., Weaver, D., Baltimore, D. and Constantini, F.: Cell 38 (1984), 647; U. Storb et al., J. Exp. Med. 164 (1986) 627; Ritchie, K. A., Brinster, R. L. and Storb, U.: Nature 312, 517 (1984); Weaver, D., Constantini, T., Imanishi-Kari, T. and Baltimore, D.: Cell 42, 117 (1985); Iglesias. A., Lamers, M. and Köhler, G.: Nature 330, 482 (1987); Neuberger, M. S., Caskey, H. M., Petersson, M., Willians, T., Surani, M. A.: Nature 338, 350 (1989)).

In some of the above-mentioned citations genes which are encoding only the light or the heavy chain of an antibody were introduced into the germ line of mice. In these investigations it turned out that the rearranged transgene inhibits the rearrangement of the endogenous immunoglobulin genes. In addition, only a relatively small expression of the introduced antibody genes (up to ca 5 to 10 µg/ml serum) was found in the transgenic mice. The expression of immunoglobulin genes after introduction into the germ line has not yet been described for other animal species.

The object of the present invention was to develop a process by which antibodies can be isolated in a high yield from transgenic animals.

The object according to the present invention is achieved by a process for the production of proteins with antibody activity in which one or more DNA sequences coding for this protein are introduced by microinjection into the male pronucleus of a fertilized ovum of a pig or rabbit, the ova are implanted in the oviduct of a pig or rabbit, the offspring are raised and the protein with the antibody activity is isolated from them in the usual way, whereby the DNA sequences used for the microinjection are free of bacterial foreign sequences.

Immunoglobulin promoter and enhancer elements are preferably used for the expression according to the present invention of the proteins with antibody activity in lymphoid cells. The genes to be expressed are subcloned in the usual way in a prokaryotic vector and multiplied in suitable host cells. The corresponding genes are isolated free of prokaryotic sequences after cleaving the vector with restriction nucleases which are suitable in each case and injected into fertilized ova. One can use circularized DNA or preferably linearized DNA for this. Expression in the transgenic animal should also occur even after deletion of intron sequences (one or several) on the genes to be expressed by in vitro mutagenesis. If complementary DNA (cDNA) is used to express light and heavy chains of an antibody, immunoglobulin promoter and enhancer sequences on the expression vectors can be cloned upstream of the cDNA to be expressed. The fusion of genomic fragments with cDNA is also possible (Gillies, S. D. et al., Bio/Technology 7 (1989) 799–804; Orlandi et al., Proc. Nat. Acad. of Sci. USA 86 (1989) 3833–3837). A further improvement in the expression of the antibody genes is also possible, if desired, by use of regulatory elements located in the non-coding regions of the antibody genes. Thus, an enhancer element located in the 3' untranslated region has been recently described for human K-genes (light chain) (Meyer, K. B. and Neuberger, M. S. EMBO J. 8 (1989) 1959–1965), an enhancer element in the 3' untranslated region has also been described for mouse λ1 chains (Bich-Thuy, L. and Queen, C., Nucl. Acids Res. 17 (1989) 5307–5321).

The term "protein with antibody activity" includes:

a) Complete antibodies of different species:

The expression is possible by introduction of the complete genes for the light and heavy chain of the antibody into fertilized pig or rabbit oocytes whereby all antibody isotypes can in principle be expressed. The heavy chain is preferably a γ-chain and the light chain is preferably a K-chain.

The antibodies can be derived from the mouse, rat or, if ova from the pig are used, also from rabbits. However, the expression of human antibodies is particularly preferred.

Human antibodies have a great diagnostic and therapeutic potential. When used for therapeutic purposes they are to be preferred over mouse antibodies or chimaerized or humanized antibodies produced by genetic engineering since an immune response of the organism is not to be expected after their therapeutic application. The construction of stable human B cell lines or hybridomas which produce antibodies in high yield is however, very difficult in practice.

Genes coding for human antibodies or cDNA of the light and heavy chains are obtainable from human hybridoma cells according to the usual methods.

The isolation of human antibodies and their therapeutic applications are described in the following citations:

James, H. and Bell, G. T., (1987), Human monoclonal antibody production. Current status and future prospects. J. Immunol. Methods 100, 5–40;

Boyd, J. E. and James, K. (1988), Human monoclonal antibodies: Their potential, problems and prospects. In: Advances in Biotechnological Processes. Vol. II. Mizraki, A. (Ed.) A. R. Liss, Inc., New York;

Larrick, J. W. and Bourla, J. M. (1986), The prospects for the therapeutic use of human monoclonal antibodies: J. Biol. Res. Mod. 5 (1986) 379–393.

b) Chimaerized and humanized antibodies

Chimaerized antibodies are understood here as molecules with variable regions of the mouse or other animal species (including D=diversity and J=joining segments) and constant regions of another species, in particular of humans. These antibodies are produced by genetic engineering, just as the humanized antibodies, in which the hypervariable CDR regions (complementarity determining regions) e.g. of a corresponding mouse or rat antibody are inserted into genes for the human light and heavy chains (=substitution of the human CDR regions by those of the corresponding mouse or rat antibody). This technique is known as CDR grafting. CDR regions are those domains of an antibody molecule which determine the affinity to the respective antigen.

In accordance with the process according to the present invention it is possible to express all possible isotypes of chimaerized antibodies in the transgenic pig or rabbit.

The isolation of chimaerized antibodies by CDR grafting is described by Jones, P. T., Dear, P. H., Foote, J., Neuberger, M. S. and Winter, G., (1986), Replacing the complementarity-determining regions in a human antibody with those from a mouse antibody, Nature 321 (1986) 522–525.

Chimaerized antibodies have great potential in the treatment of malignant diseases. Here, the antibodies recognize epitopes on antigens specific for tumour cells (Sun et al., Proc. Natl. Acad. Sci. USA 84 (1987) 214–218; Nishimura, Y. et al., Cancer Res. 47 (1987), 999–1005).

c) Heterobispecific antibodies:

Heterobispecific antibodies have great therapeutic potential for example in the elimination of cells infected with viruses. A heterobispecific antibody recognizes e.g. an epitope on antigens present on the cell surface and on cytotoxic T-cells (Gilliland, L. K., Clark, M. R. and Waldmann, H.: Proc. Natl. Acad. Sci. USA 85 (1988) 7719–7723; Staerz, U. D., Yewdell, J. W. and Bevan, M.: Eur. J. Immunol. 17 (1987) 571–574). A process for the production of heterobispecific antibodies by genetic engineering was described in EP-A 0 388 964. The expression in the transgenic pig or rabbit requires the isolation of the genes for the light and heavy chains of both antibodies and subsequent injection into fertilized ova. In this process it is not absolutely essential that the two antibodies have the same isotype (e.g. IgG1). According to the process according to the present invention it is possible to produce heterobispecific antibodies having different isotypes from transgenic pigs or rabbits and to investigate their properties with regard to CDC (complement dependent cytotoxicity) and ADCC (antibody-dependent cell-mediated cytotoxicity).

d) Antibody fragments:

Partial domains of antibodies such as e.g. F(ab')$_2$, Fab fragments, the Fc part or Fv fragments also come into consideration for expression in transgenic pigs. Such antibody fragments can be obtained if, instead of the complete DNA sequences coding for antibody molecules, only the partial sequences which code for the respective antibody fragment are microinjected into the transgenic pig or rabbit. For the definition of the individual fragments refer to: Roitt, I., Brostoff, J. and Male, D: Immunology. Gower Medical Publishing, London New York, 1985. F(ab')$_2$ or Fab fragments are important for diagnostic applications such as for example in tumour imaging.

e) Fusion proteins with domains of antibody molecules:

This term is understood to encompass fusions between the antigen binding part of an antibody and the signal transducing region (transmembrane domains and cytoplasmic domains) of other members of the immunoglobulin superfamily (e.g. T-cell receptor or Fc receptors). Such molecules could become of great practical importance as possible biosensors. The expression of heterologous fusion proteins is also possible according to the process according to the present invention by microinjection of the corresponding DNA sequences into oocytes of the pig or rabbit. For example, the antigen binding domain of an antibody can be fused with a domain which after antigen binding, mediates an enzymatic function (e.g. tyrosine-kinase domain of the insulin receptor or of the EGF receptor or guanylate cyclase domain of the ANF receptor).

Also therapeutically relevant fusion proteins, such as fusions of domains of the CD4 antigen, the receptor for the HIV virus on human T lymphocytes and domains of antibody molecules which mediate important effector functions (e.g. complement binding, cell lysis) can be expressed according to the process according to the present invention in high yields in transgenic pigs.

f) Mutated antibodies:

These include antibodies which, by means of genetic manipulations, have an improved affinity to the antigen compared to the initial antibody. These also include antibodies in which the complement binding properties or the binding characteristics with respect to Fc receptors on macrophages and monocytes have been altered (by genetic manipulation) as well as antibodies with altered cytolytic properties. This group of antibody molecules can also be expressed in transgenic pigs or rabbits according to the process according to the present invention.

Apart from the isolation of antibodies from serum it is also possible to effect an immunization of transgenic pigs or rabbits by the process according to the present invention. Genes for antibodies against certain antigens, in particular antigens which cause diseases which are dangerous to these animals e.g. influenza or swine fever, can be very efficiently introduced into the germ line of these animals using the process according to the present invention. In this manner one can breed animals which are resistant to certain infections.

Furthermore, the secretion of therapeutically relevant proteins into milk is also possible by means of the process according to the present invention.

Antibody molecules of the IgA class can be secreted into milk (secretory IgA=sIgA). By fusion with IgA it is possible to also secrete other proteins e.g. coagulation factors such as factor VIII or factor IX or enzymes such as e.g. human tissue-type plasminogen activator into the milk of transgenic animals. By incorporation of corresponding enzymatic cleavage sites between the secretory antibody and the fusion partner (e.g. collagenase, factor Xa), the authentic molecule can be obtained after isolation from the milk and subsequent enzymatic cleavage.

It is apparent from the previous exposition that the present invention also encompasses a process for the production of transgenic animals in which one or several DNA sequences coding for a protein with antibody activity which are free of bacterial foreign sequences are introduced into the male pronucleus of fertilized oocytes of a pig or rabbit, the oocytes are implanted in the oviduct of a female animal and the offspring are raised. For example one can use DNA sequences which code for proteins with an antibody activity which is directed towards an antigen which causes a disease which is dangerous for the respective animal species (pig or rabbit). Such animal diseases are known to the expert as well as the antigens which cause them. With the aid of these known antigens, antibodies may be produced in the usual way whose DNA sequence can then be obtained in a known way (e.g. by screening a gene bank). Subsequently these DNA sequences coding for these antibodies can be used for the production of transgenic animals according to the process according to the present invention. In this way transgenic animals can e.g. be produced which have an immunity against certain diseases.

A further subject matter of the present invention is the transgenic animal (i.e. a rabbit or pig) which is obtainable by a process according to the present invention. Examples of transgenic animals according to the present invention are for instance those which produce the antibody A20/44; the latter is an anti-idiotypic antibody which is described in EP-A 0 388 964.

The following examples should further elucidate the invention in conjunction with FIG. 1.

BRIEF DESCRIPTION OF THE FIGURES

FIG. 1 shows the antibody genes used for the microinjection.

EXAMPLE 1

Production of Antibody DNA Sequences

The starting vectors are the plasmids pBMS1 (DSM 5229) and pBMS2 (DSM 5230) which are described in EP-A 0 388 964 (process for the production of heterobispecific antibodies). The vectors contain the K and γ1 genes of a mouse antibody which are in different orientations to one another. These genes were isolated from a hybridoma cell line which secretes an IgG1 antibody denoted A20/44 (Sablitzky, F., Wildner, G. and Rajewsky, K.: EMBO J. 4 (1985) 345–350; Sablitzky, F., Weisbaum, D. and Rajewsky, K.: EMBO J. 4 (1985) 3435–3437; Kocks, C. and Rajewsky, K.: Proc. Natl. Acad. Sci. USA 85 (1988) 8206–8210). A20/44 is an anti-idiotypic antibody which is directed towards an antibody specific for the hapten NP (4-hydroxy-3-nitro-phenylacetate). The latter antibody has a λ-chain as the light chain and a $\gamma_{2a}$-chain as the heavy chain (IgG2a).

The vectors described in EP-A 0 388 964 contain the K gene as a 5.5 kb SaII fragment, the γ1 gene as a 9.25 kb SaII fragment. In addition, the vectors contain expression cassettes for the phosphotransferase neo and mouse dihydrofolate reductase under the control of the early promoter of SV40.

pBMS1 and pBMS2 (each containing 3 SaII sites) were partially cleaved with SaII, treated with nuclease S1 (1 µg of DNA partially cleaved with SaII is incubated with 10 units S1 nuclease for 60 minutes at 30° C. in 50 mmol/l sodium acetate, pH 4.5; 1 mmol/l $ZnSO_4$ and 0.5% by weight glycerol), the linearized plasmid was isolated on an agarose gel of low-melting point and the ends were subsequently ligated with T4 ligase. The ligation preparations were transfected into the E.coli strain HB101 and ampicillin resistant (50 µg/ml) colonies were isolated on agar plates. By analysis with restriction endonucleases, those plasmids were determined in which the SaII site located between the K and the γ gene has been deleted by the manipulation described above. The plasmids obtained are denoted pBMS1 (ΔSaII) and pBMS2 (ΔSaII).

pBMS1 (ΔSaII) and pBMS2 (ΔSaII) were cleaved with SaII and the SaII fragment, which contains the K and γ1 gene of the antibody was isolated on an agarose gel of low-melting point and subsequently dissolved in 10 mM TRIS HCl, pH 7.5, 0.25 mM EDTA.

By this means the antibody genes were isolated free of vector sequences for the subsequent microinjection experiment (see FIG. 1).

EXAMPLE 2

Production of Transgenic Mammals

The production of transgenic mammals encompasses the production of an injectable DNA solution, the isolation of fertilized ova and embryos, the microinjection of the DNA solution into pronuclei or nuclei, the transfer of the injected zygotes into synchronized recipient animals and the examination of the born animals for integration. For the individual mammalian species such as mouse, rabbit and pig there are some species-specific differences which have to be thereby taken into account when preparing the donor and recipient animals, and in the isolation and transfer of the embryos as well as in the microinjection.

1. Production of an injectable DNA solution

After isolation of the DNA fragments and determination of the DNA content, the DNA solution is diluted with Tris buffer such that the solution contains up to 1000 copies of the gene construct per pico liter of solution. All solutions used for the production of the DNA microinjection solution must be free of particulate impurities in order to avoid blockage of the injection pipettes.

2. Isolation of the embryos

In order to increase the yield of embryos the donor animals are usually superovulated.

Mouse

Female mice which are at least 6 weeks old are injected with 5–10 IU PMSG (pregnant mare serum gonadotrophin) to induce superovulation. 48 hours later they receive 5–10 IU HCG (human chorionic gonadotrophin) and are mated with fertile male mice. On the next morning the plaque-positive mice are killed and the oviducts are excised after opening the abdominal cavity. The embryos are obtained by tearing open the ampulla with fine forceps or by rinsing the oviducts and transferred into embryo culture medium to which hyaluronidase had been added. The ova are washed after removing the cumulus cells and cultivated until the microinjection.

Rabbit

Sexually mature donor rabbits receive a single dose of 10–40 IU PMSG (pregnant mare serum gonadotrophin) per kg body weight for the superovulation. Preceding this superovulation the animals should either be kept singly for 21 days or pre-synchronised (120 IU HCG or 0.8 µg GnRH (gonadotrophin-releasing factor)). 72 to 76 hours after the PMSG injection the rabbits are twice artificially inseminated or mated naturally at an interval of one hour. Immediately afterwards they receive 120–180 IU HCG i.v. for the induction of ovulation. The embryos are isolated 19 to 21 hours after the copulation by slaughtering the donor rabbits. The embryos are isolated by flushing the oviducts with culture medium for rabbit embryos (BMS+20% FCS or PBS+20% FCS) from the infundibulum towards the uterus-horn end. If necessary the cumulus oophorus which is still present is removed by hyaluronidase treatment. The embryos are washed and cultured until the microinjection.

Pig

In the case of the pig, young pre-puberal gilts weighing 60 to 90 kg can also be used for obtaining embryos. On day 0 the donor animals are transferred to new pens and 1250 IU PSMG is administered in the evening. The ovulation is induced 72 hours later with the aid of 750 IU HCG. 24 and 36 hours after the HCG administration the animals are inseminated. The embryos are isolated 24 to 27 hours after the insemination. In order to surgically isolate the embryos the animals are anaesthetized with 160 mg Azaperon (Stressnil) and 400 mg Metomidate hydrochloride (Hypnodil). After preparing the operating area, the skin is opened medially at the level of the last pair of teats with a ca. 10 cm long incision and the uterus, oviduct and ovary are exteriorized. A blunt perforation of the uterus is made ca. 5 cm caudal to the utero-tubal junction so that a ca. 5 cm class cannula can be inserted into the lumen and fixed there. A 8 cm long curved eye cannula which is connected to a ca. 30 cm long rubber tube is inserted through the infundibulum into the oviduct and fixed there. The oviduct is flushed with 50 ml PBS solution. The flushing liquid is collected in a petri dish and examined for embryos. The isolation of embryos can also take place after the slaughter of the donor animals.

3. Microinjection of the DNA solution

An inverse microscope (Zeiss, ICM 405), two Leitz micromanipulators and an injection apparatus (Eppendorf) are used for the microinjection. One of the manipulators carries a holding pipette by which the embryo can be held in position by reduced pressure. On the second micromanipulator the injection pipette filled with the DNA solution is fixed in a nanostepper and connected to the injection instrument. The tip of the injection pipette has a diameter of one to two µm. For the microinjection, the tip of the pipette is pushed forward through the zona pellucida, the cell membrane and the nuclear membrane into the lumen of the nucleus and ca. 1 to 2 pl DNA solution are deposited there. The increase in volume of the pronucleus signalizes a successful microinjection. Sometimes the nuclei of embryos are also microinjected in the two-cell stage.

The oocytes and embryos of most species of farm animals (pig, cattle), in contrast to the mouse or rabbit, have to be pretreated in order to visualize the pronuclei and nuclei (centrifugation at 15000 g for 3 to 5 minutes). The microinjection takes place in a drop of medium on a cover plate or in a so-called injection chamber. After the microinjection the oocytes or embryos are cultured up to the transfer.

4. Transfer of microinjected oocytes

Mouse

Recipient mice are mated overnight with vasectomized male mice in order to induce a pseudo-pregnancy. Plaque positive mice are selected and anaesthetized for the transfer. The exteriorized bursa ovarica is opened with fine forceps and the embryos (10–15 per side) which are drawn up into a transfer pipette are transferred into both oviducts. The young are born 20 to 21 days after the transfer.

Rabbit

Recipient rabbits are kept singly in individual cages 21 days before the expected date for the synchronization of the cycle and receive 120 IU HCG or 0.8 µg GnRH i.m. for the induction of a pseudo-pregnancy. On the day before the transfer the recipient rabbits receive 120 IU HCG i.v. for the induction of ovulation. For the transfer the rabbits are anaesthetized with 0.4 ml Rompun, 2% per kg/body weight, and 0.8 ml Ketamine, 10% per kg/body weight. After preparing the operating area and emptying the bladder by transabdominal pressure, the rabbits are tied down in a dorsal position and fixed in an oblique position. The abdominal cavity is opened for a length of ca. 4–5 cm directly caudal to the navel. The ovary, oviduct and cranial uterine horn are exteriorized and, after checking the reaction of the ovary, the microinjected embryos are transferred with the aid of a transfer pipette ca. 2 to 2.5 cm deep into the ampulla of the oviduct. Between 8 and 15 embryos are transferred per side. After closing the abdominal cavity the operation wound is protected by a surgical skinflap suture. The young are born 29 to 31 days after the transfer.

Pig

Pre-puberal gilts can also be used as recipient animals. The recipient animals receive 750 IU PMSG 12 hours after the donor animals and after a further 72 hours 750 IU HCG. This 12 hour difference in synchrony between donor and recipient animal improves the chances of survival of the embryos after transfer. The recipient animals are observed for their receptive period parallel to the insemination of the donor animals. 135 to 136 hours after the start of the programme (hour 0=PMSG injection in the donor animals) the embryo transfer takes place. All injected embryos (35–45 of them) are transferred by surgical transfer into an oviduct of a recipient pig. The embryos distribute themselves evenly by spacing between both uterine horns. A new method also enables the non-invasive transfer of embryos into the pig uterus. The piglets are born 113 to 116 days after the transfer.

5. Investigation of integration

In order to investigate the integration of the injected DNA, tissue samples (tail tissue, blood or biopsy) must be obtained from the born animals. High molecular weight genomic DNA is isolated from these tissue samples. The detection of integration is carried out by slot blot, dot blot or Southern blot analyses.

Positive animals (animals with an integration of the gene construct) are raised and after reaching breeding maturity they are mated with non-transgenic mating partners. The offspring which result from these matings are examined for whether they have inherited the transgene from their transgenic parent. Homozygous transgenic F2 offspring are then bred by mating hemizygous transgenic animals.

In order to examine expression, serum is obtained from transgenic animals after collecting blood. Blood is taken by puncture of the retrobulbar eye plexus (mouse), the ear vein (rabbit), or the jugular vein (pig) or from other accessible veins or when the animals are killed.

EXAMPLE 3

Determination of the Antibody Titre in the Serum of the Transgenic Animals

The method for the determination of the antibody titre is described in EP-A 0 388 864. Microtitre plates were coated with antibodies against the hapten NP (4-hydroxy-3-nitrophenylacetate). This antibody is of the type IgG 2a (the light chain is a λ chain, the heavy chain is a γ2a chain). The coating buffer consisted of 0.2 mmol/l carbonate/bicarbonate, pH 9.4. After 2 hours the plates were incubated with a re-coating buffer (50 mmol/l HEPES, 0.15 mol/l NaCl, 1% crotein C, pH 7.0). All reactions were carried out at room temperature while shaking. The calibration curve was established with a stock solution containing an antibody A20/44 (IgG 1) (dilution series). The calibration samples and the sera were diluted with incubation buffer (50 mmol/l HEPES, 0.15 mol/l NaCl, 1% crotein C, pH 7.0, 0.2 mol/l di-sodium tartrate, 0.75% polyethylene glycol (PEG), 0.5% Pluronic®F 68, 0.75% PEG 40000, 0.01% phenol) and incubated for 2 hours at room temperature. After aspirating the wells and washing twice with incubation buffer, a 1 hour incubation with conjugate (conjugate of Fab fragments of the antibody, which is directed towards NP, and peroxidase (POD)) was carried out. For this the conjugate was diluted in the incubation buffer to 150 mU/ml POD activity. After aspirating and washing the wells three times with wash buffer (50 mmol/l HEPES, 0.15 mmol/l NaCl, 0.1% Pluronic®F 68, pH 7.0) they were reacted for 60 minutes with ABTS® (2,2'azino-di-[3-ethyl-benzthiazoline sulfonate (6)] as substrate. The absorbance was measured in a photometer (ELISA reader) at 405 nm against 490 nm. The concentration of the samples was determined via the standard calibration curve.

TABLE

Antibody titre in the serum of transgenic animals

| mouse no. | µg/ml | rabbit no. | µg/ml | pig no. | µg/ml |
|---|---|---|---|---|---|
| 970-28 | 3 | 2644 | 200 | 5814 | 1000 |
| 970-29 | 7 |  |  | control | 0 |
| 970-31 | 18 | control | 0 |  |  |
| 970-32 | 10 |  |  |  |  |
| 970-33 | 18 |  |  |  |  |
| 970-54 | 30 |  |  |  |  |
| 970-55 | 3 |  |  |  |  |
| 970-56 | 18 |  |  |  |  |
| 970-59 | 3 |  |  |  |  |
| 974-1 | 27 |  |  |  |  |
| 974-2 | 29 |  |  |  |  |
| 974-3 | 18 |  |  |  |  |
| 974-4 | 4 |  |  |  |  |
| 974-8 | 18 |  |  |  |  |
| 974-9 | 100 |  |  |  |  |
| 974-10 | 45 |  |  |  |  |
| 974-11 | 20 |  |  |  |  |
| 974-12 | 120 |  |  |  |  |
| 974-13 | 60 |  |  |  |  |
| 974-14 | 15 |  |  |  |  |
| control | 0 |  |  |  |  |

The investigated mice are offspring of both the seropositive mice 970 and 974. A series of offspring were seronegative with respect to the introduced antibody specificity. These are not listed in Table 1. After microinjection all 39 rabbits were examined for expression. One animal expressed the desired antibody specificity in serum. Two transgenic pigs (1 still birth) were obtained. The live offspring expressed the desired antibody in a surprisingly very high concentration in serum (1000 µg/ml).

EXAMPLE 4

Characterization of the Expressed Antibody in Pig Serum a) Isoelectric focussing and immuno-fixation IEF was carried out on a Phast-Gel-System (Pharmacia) according to the instructions of the manufacturer. The sera of the transgenic and of the control pig were diluted 1:1000 and applied to the gel under non-denaturing conditions. The pH gradient on the gel (pH 5–8) was visualized by calibration proteins (Pharmacia). The running time of the gel was 30 minutes. Subsequently it was incubated for 45 minutes with 100 µg of a polyclonal antibody (sheep anti-mouse Fcγ) in a volume of 150 µl and covered with a cellulose acetate strip. The non-reacting proteins were removed by washing with 50 mmol/l potassium phosphate buffer, 0.15 mol/l NaCl, 0.05% Tween®, pH 7.2 by shaking overnight. The immunocomplexes were subsequently visualized by silver staining (Pharmacia kit). Antibody A20/44 which was purified from ascites was applied as a control.

It turned out that the same characteristic bands can be identified in the serum of the transgenic pig as with the purified antibody A20/44. These characteristic bands were not detectable in the serum of the control animal.

b) Purification of antibody A20/44 from the serum of the transgenic pig

A20/44 is an anti-idiotypic antibody against an antibody (IgG2a) which is directed towards the hapten NP. The latter was purified from ascites and coupled to cyanogen-bromide-activated Sepharose (Pharmacia) according to the instructions of the manufacturer. Antibody A20/44 was immunoadsorbed to an affinity column prepared in this way after application of 100 ml serum from the transgenic pig, eluted and subsequently its protein and chemical content was characterized. Its properties corresponded with those of the antibody A20/44 purified from ascites fluid.

We claim:

1. Process for the production of antibodies, comprising the steps of:

introducing at least one DNA sequence coding for a rearranged antibody, said DNA sequence being free of bacterial foreign sequences, into the male pronucleus of a fertilized ovum of a pig or rabbit by microinjection, implanting the ovum in the oviduct of a pig or rabbit to obtain offspring, raising the resulting transgenic animal, and isolating the rearranged antibody from the transgenic animal wherein the rearranged antibody is produced at a concentration of at least 200 µg/ml.

2. Process according to claim 1, wherein the DNA sequence also includes immunoglobulin promoter and enhancer sequences.

3. Process according to claim 1, wherein the DNA sequence used for the microinjection is linear.

4. Process according to claim 1, wherein the rearranged antibody is a complete native antibody.

5. Process according to claim 4, wherein the antibody has a γ-heavy chain and a K-light chain.

6. Process according to claim 1, wherein the rearranged antibody is a chimerized antibody.

7. Process according to claim 1, wherein said rearranged antibody is fused with a further polypeptide.

8. Process according to claim 1, wherein the rearranged antibody is a mutated antibody.

9. Process for the production of antibodies, comprising the steps of:

introducing at least one DNA sequence coding for a rearranged antibody, said DNA sequence being free of bacterial foreign sequences, into the male pronucleus of a fertilized ovum of a pig or rabbit by microinjection, implanting the ovum in the oviduct of a pig or rabbit to obtain offspring, raising the resulting offspring to breeding maturity, breeding the offspring with non-transgenic mating partners to product F1 progeny, raising the F1 progeny to breeding maturity,
crossbreeding the F1 progeny to produce F2 progeny, and
isolating the antibodies from the F2 progeny,
wherein the antibodies are produced at a concentration of at least 200 µg/ml.

10. The process according to claim 1, wherein said ovum is implanted in the oviduct of a pig and said rearranged antibody is produced at a concentration of at least 1,000 µg/ml.

* * * * *